United States Patent [19]

Crouther et al.

[11] Patent Number: 5,554,127
[45] Date of Patent: Sep. 10, 1996

[54] SYRINGE NEEDLE THIMBLE CAP AND METHOD OF USE THEREOF

[75] Inventors: Ronald Crouther, Chesterfield; Douglas L. Stenslokken, Ballwin; Eugene E. Weilbacher, Ellisville, all of Mo.

[73] Assignee: Sherwood Medical Company, St. Louis, Mo.

[21] Appl. No.: 321,000

[22] Filed: Oct. 11, 1994

[51] Int. Cl.$^6$ .................................................. A61M 5/32
[52] U.S. Cl. ........................ 604/192; 604/263; 206/366
[58] Field of Search ................................. 604/192, 187, 604/198, 263, 199, 122; 206/365, 366

[56] References Cited

U.S. PATENT DOCUMENTS

| | | | |
|---|---|---|---|
| 4,043,334 | 8/1977 | Brown et al. | 128/215 |
| 4,085,737 | 4/1978 | Bordow | 128/2 F |
| 4,248,246 | 2/1981 | Ikeda | 604/263 |
| 4,317,455 | 3/1982 | Akhavi | 128/765 |
| 4,340,067 | 7/1982 | Rattenborg | 128/763 |
| 4,380,292 | 4/1983 | Cramer | 206/366 |
| 4,424,817 | 1/1984 | Williams | 128/766 |
| 4,619,651 | 10/1986 | Kopfer et al. | 604/415 |
| 4,675,017 | 6/1987 | Sato | 604/405 |
| 4,728,321 | 3/1988 | Chen | 604/110 |
| 4,735,311 | 4/1988 | Lowe et al. | 206/365 |
| 4,743,243 | 5/1988 | Vaillancourt | 604/405 |
| 4,755,170 | 7/1988 | Golden | 604/52 |
| 4,769,026 | 9/1988 | Strung | 604/415 |
| 4,775,376 | 10/1988 | Strung | 604/415 |
| 4,781,683 | 11/1988 | Wozniak et al. | 604/110 |
| 4,982,842 | 1/1991 | Hollister | 206/365 |
| 5,078,695 | 1/1992 | Farrar et al. | 604/192 |
| 5,084,027 | 1/1992 | Bernard | 604/192 |
| 5,085,647 | 2/1992 | Henderson et al. | 604/192 |
| 5,088,996 | 2/1992 | Kopfer et al. | 604/415 |
| 5,098,404 | 3/1992 | Collins | 604/199 |
| 5,125,415 | 6/1992 | Bell | 128/766 |
| 5,147,309 | 9/1992 | Hemmerich et al. | 604/122 |
| 5,209,733 | 5/1993 | Lever et al. | 604/192 X |
| 5,230,428 | 7/1993 | McShane | 206/363 |
| 5,232,454 | 8/1993 | Hollister | 604/192 |
| 5,232,455 | 8/1993 | Hollister | 604/192 |

*Primary Examiner*—John D. Yasko
*Attorney, Agent, or Firm*—Gene B. Kartchner; David A. Warmbold; Montgomery W. Smith

[57] ABSTRACT

A syringe needle thimble cap and its method of use is shown such that the thimble cap has a porous plastic, hydrophilic core captured within a cylindrical cap member for use with an arterial blood gas syringe barrel and needle assembly. The syringe needle thimble cap has a generally thimble-shaped cap with a proximal opening. The porous plastic core material is positioned within the thimble cap distally to the proximal opening, and the core material is held in place by an inwardly extending ring to prevent its removal. An open or hollow space is created distally to the porous material which is otherwise bounded by the interior surfaces of the thimble cap.

19 Claims, 2 Drawing Sheets

SYRINGE NEEDLE THIMBLE CAP AND METHOD OF USE THEREOF

FIELD OF THE INVENTION

This invention relates generally to an apparatus for protecting the sharp needle tip of a medical syringe, and more particularly to an apparatus and method for catching fluid purged from the needle of a syringe while capturing the tip of the needle for safe disposal of the needle.

BACKGROUND OF THE INVENTION

The use of syringes for the hypodermic withdrawal of blood from a patient's body through a hollow needle detachedly forming a part of a syringe is commonplace in modern medicine. One reason to take blood from a patient is to obtain an arterial blood gas sample. Air is almost always included within the syringe barrel or needle after filling the syringe barrel with blood. For example, aspiration of a sample through a needle or the incomplete filling of a syringe may draw air into the syringe. There are many instances in which such air can contaminate an arterial blood gas sample. In taking an arterial blood gas sample, the purpose is to evaluate the patient's blood gas levels (i.e., carbon dioxide and oxygen) or to evaluate other variables which depend upon blood gas levels (i.e., pH levels), therefore the introduction of air into the sample would serve to alter the true concentrations in the blood and cause subsequent analysis of data to be misleading. It is therefore desirable to remove any air from the blood sample as quickly as possible after removal of the blood from the patient's body.

Accordingly, one technique for removing air from a freshly-filled syringe is to tilt the syringe upward so that the air bubbles rise to the top of the syringe barrel and the plunger is advanced into the barrel to purge the air through the needle tip. Although this technique works well in removing air from the syringe body and needle, it may also cause some blood to be expelled from the tip of the needle. The blood may be expelled either if the plunger is pushed too aggressively or if blood is trapped by capillarity in the uppermost portion of the luer, needle hub or needle.

Typically, the purged air and liquid spray from the needle would be simply squirted into the air or into a pad of gauze material. However, with the great concerns today about the transmission of various diseases such as AIDS and hepatitis, great care must be taken in the removal of such blood spray from an arterial blood gas sample and further in the handling and disposal of hypodermic syringe needles used with such syringe systems.

Many prior art patents dealing with the blood sample air-contamination problem concentrated on expelling contaminating air from the syringe while the syringe was being filled with the patient's blood. U.S. Pat. Nos. 3,978,846 and 4,340,067 disclose devices incorporating self-sealing hydrophilic filters into the body of the syringe. When dry, a self-sealing type hydrophilic filter allows air to pass through it and out of the syringe. The syringe-filter system fills with blood because a pressure differential between the luer opening and the filter is created by the patient's arterial pressure. This air pressure differential helps force air through the filter and out of the syringe. When all of the air is expelled, the leading edge of the blood contacts the filter. When wetted by the blood, the self-sealing nature of the filter causes it to expand and prohibit passage of both air and liquid. However, the utility of these type of self-sealing hydrophilic systems does not extend to post filling contaminations because the already wetted filter will no longer pass air and so it can not be utilized to purge any remaining air or air introduced at later times. Also, such filters have not always self-sealed in the proper manner thereby allowing blood to seep out of the plunger end of the syringe body possibly causing dangerous contamination of medical personnel.

U.S. Pat. Nos. 4,769,026 and 4,775,376 to Strung disclose syringe purging devices that address the problems of post filling contamination. These devices utilize separate containers which are either airtight or are equipped with hydrophobic filters. Hydrophobic filters allow for the passage of air but not liquid. Various embodiments of these patents also include a deactivating substance for neutralizing the hazardous fluids which are to be injected into the container. In use, the container and syringe are attached in an airtight fit, air and blood from the syringe are injected into the separate container by advancing the syringe plunger until the air has been evacuated from the syringe. However, such a device is overly complicated for the uses intended for the present invention. An airtight chamber is neither necessary nor desirable for the present invention. Furthermore, a deactivating substance involves an unnecessary complication and expense.

U.S. Pat. No. 5,125,415 to Bell discloses a syringe tip cap utilizing a self-sealing hydrophilic filter in a separate chamber for allowing for the purging of air from the syringe body. However, the syringe tip cap disclosed in Bell can be used only after the needle and hub assembly has been removed from the syringe body. Typically, the sequence of events by a nurse technician or other medical personnel in taking an arterial blood gas sample would be as follows. First, the technician would remove the blood filled needle and syringe barrel assembly from the patient's arm or any other injection site with one hand while depressing the injection site with the fingers of their other or second hand. The needle and syringe barrel assembly is set aside while the patient's arm is properly bandaged. Next, the technician would remove the needle and needle hub from the syringe barrel and properly dispose of them into a protective sharps container. Then, the syringe tip cap would be attached to the distal end of the syringe barrel, the syringe barrel would be held in an upside down position or held with the distal end pointing upwardly while the technician advances the plunger to purge any air bubbles with attendant liquid blood spray out of the syringe barrel and into the absorbent filter of the syringe tip cap.

The above sequence of events is undesirable in that the air bubbles were allowed to remain in the blood sample for a significant period of time while the technician was bandaging the patient's arms and removing and disposing of the needle and hub assembly into a protective sharps container. It is possible that the blood sample would be significantly contaminated by the air existing within the blood sample so as to provide erroneous blood gas levels such that subsequent analysis of this data to be misleading.

SUMMARY OF THE INVENTION

It is an object of the present invention to provide a protective cover for a previously used syringe needle which substantially aids in avoidance of accidental needle sticks to medical personnel using the syringe assembly.

It is a further object of the present invention to provide a syringe needle thimble cap for placement over a previously used syringe needle to allow air bubbles and any attendant liquid and/or blood spray to be injected into the thimble cap to prevent external contamination of the surgical field or to medical personnel.

It is another object of the present invention to provide a syringe needle thimble cap for use with an arterial blood gas sample syringe barrel and needle assembly so that any air bubbles within the blood filled syringe barrel may be purged into the syringe needle thimble cap without external contamination of the surgical field or to medical personnel, and to protect the needle tip to prevent accidental needle sticks of medical personnel.

It is another object of the present invention to provide a syringe needle thimble cap that can be installed on a syringe barrel and needle and utilized to purge any air bubbles out of the syringe body by use of only one hand of a medical technician using such syringe barrel and needle assembly.

It is yet another object of the present invention to provide a syringe needle thimble cap for use with an arterial blood gas sample syringe barrel and needle assembly which can be installed on the needle assembly via the use by one hand of a medical technician such that the syringe barrel may be inverted and any air bubbles evacuated therefrom without such technician removing their other hand from the injection site on the patient's body.

These and other objects are realized in the presently preferred embodiment of a syringe needle thimble cap having a porous plastic, hydrophilic-type core captured within its boundaries for use with a standard arterial blood gas syringe barrel and needle assembly. The syringe needle thimble cap includes a generally thimble-shaped rigid plastic cap having a proximal opening. It is preferable for the plastic material of the rigid cap to be clear or substantially clear to allow a medical technician to observe the needle point within the thimble cap. The porous plastic core material is positioned within the thimble cap distally to the proximal opening, and the core material is held in place by an inwardly extending ring or lip to prevent the removal of the porous plastic material. The core material is slightly compressible to allow it to be positioned within the thimble cap such that the inwardly extending ring compresses the core provide a snug fit. Additionally, the porous plastic material occupies only a portion of the space within the thimble cap such that an open or hollow space is created distally to the porous material and otherwise the open space is bounded by the interior surfaces of the thimble cap.

The proximal opening of the thimble cap allows for the introduction of the needle point and shaft of the needle assembly into the porous plastic material of the thimble cap. The needle point is pushed completely through the porous plastic material by the medical technician which gives the technician a feel as to when the needle point has been penetrated through the porous plastic material sufficiently so that its needle point is positioned within the open space of the thimble cap. The plunger of the syringe barrel may now be advanced while holding the syringe barrel and needle assembly with thimble cap affixed thereto in an inverted position such that the needle point is pointing in an upwardly direction. When the air bubbles are expelled into the open space of the thimble cap, a small amount of blood is also expelled into the thimble cap which is absorbed by the porous plastic material. Thus, when the syringe needle thimble cap of the present invention is placed over the syringe needle as discussed above, the thimble cap protects the medical technician from needle stick injuries and absorbs any potentially hazardous blood that is expelled from the syringe barrel while letting any air pass through the porous material. Furthermore, when the red blood spray is injected into the core material this provides the medical technician with a visual indication of when all the air has been expunged from the syringe barrel and needle assembly.

According to another aspect of the present invention, an improved method for quickly purging air bubbles from a syringe containing a patient's arterial blood gas blood sample so that such air bubbles do not contaminate the results obtained from later analysis of such blood sample is also disclosed. The method includes the steps of: withdrawing a filled arterial blood gas sample syringe barrel and needle assembly from a patient's arm with one hand while depressing the injection site with the other hand of a medical technician taking a patient's blood sample; stabbing the needle point into a syringe needle thimble cap of the present invention and inverting the syringe barrel, needle assembly and attached thimble cap so that the needle assembly is pointing in an upwardly direction and any air bubbles contained within the syringe barrel have gravitated towards the needle assembly; manually operating the syringe to purge air and/or excess liquid blood from the syringe barrel and needle assembly while still depressing the injection site on the patient's arm or other injection site with one hand; retaining any ejected liquid blood within the thimble cap; setting the syringe barrel and needle assembly aside while properly bandaging the patient's injection site; removing the needle assembly with protective thimble cap attached over the end of the needle point from the syringe barrel containing the arterial blood gas sample; and discarding the needle assembly with thimble cap into a protective sharps container.

Alternatively, the method for purging a syringe barrel may include setting the blood filled syringe barrel and needle assembly aside immediately after withdrawing the syringe barrel and needle assembly from the patient's arm and stabbing the needle point into the thimble cap so that the medical technician can properly bandage the patient's arm, and then allowing the technician to follow through with the steps of purging the air bubbles from the syringe barrel as discussed above. In either method, the medical technician would then cap the syringe barrel and send the blood sample to the lab for analysis.

DETAILED DESCRIPTION OF THE INVENTION

Figure 1:
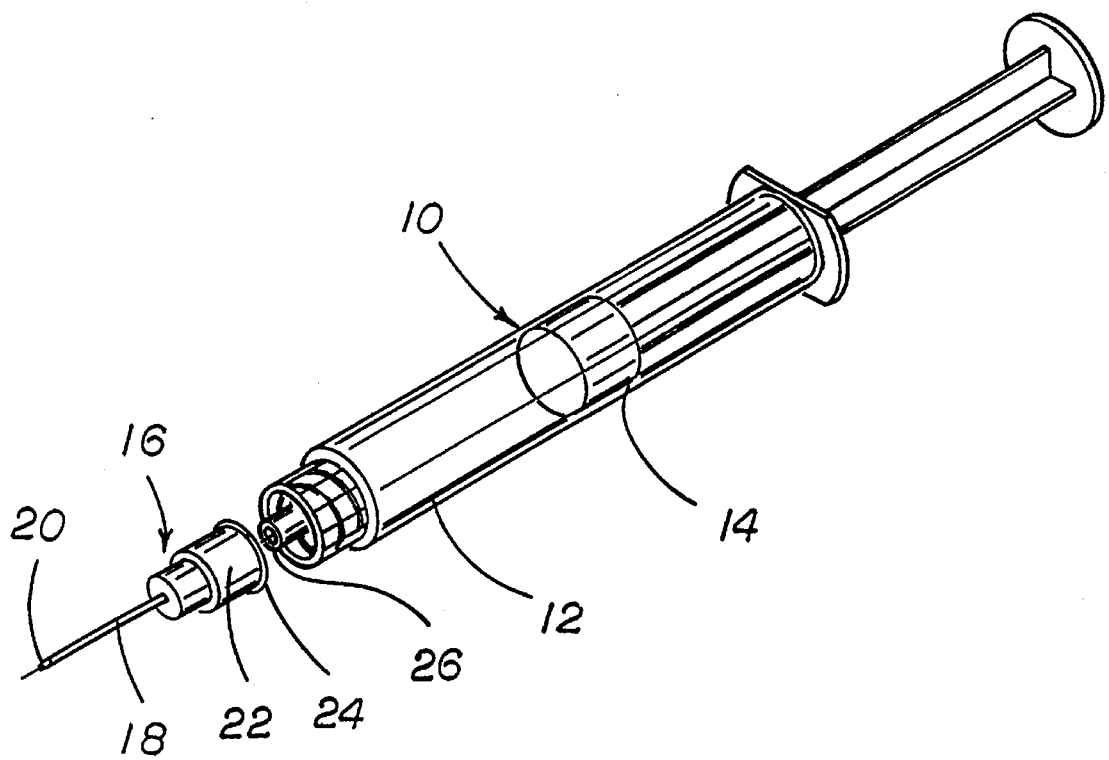
FIG. 1 is a partially exploded view of a standard syringe barrel, plunger and needle assembly wherein the needle assembly is shown separated from the syringe barrel.
Figure 2:
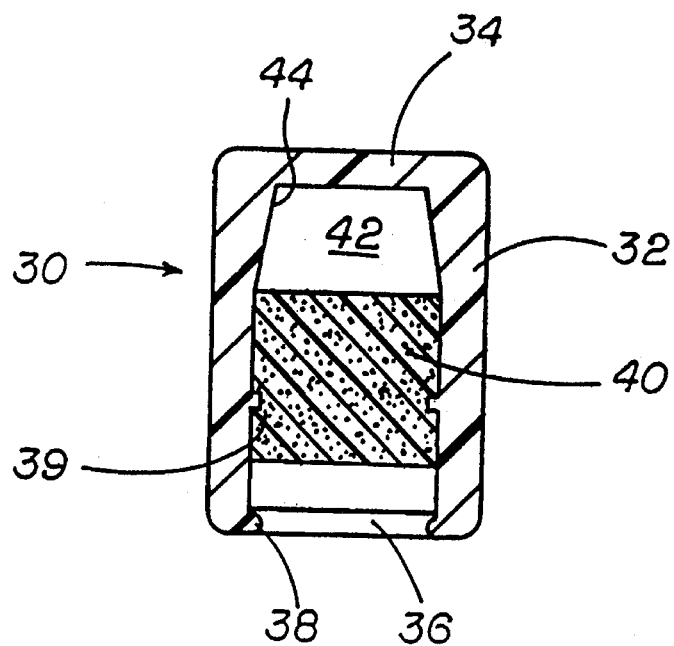
FIG. 2 is a cross-sectional view of the syringe needle thimble cap of the present invention.

Referring now to FIG. 2 of the drawings, a syringe needle thimble cap according to the present invention is shown and denominated by the reference numeral 30. The syringe needle thimble cap 30 is designed to cooperate with a standard hypodermic syringe 10. As shown in FIG. 1, syringe 10 includes a syringe barrel 12 fitted with a plunger 14 slidably received therein so that the inside walls of the barrel and the outer edge of the plunger produce a tight fit around the circumference of the plunger 14. The syringe barrel 12 is further provided with a needle assembly 16 having a hollow needle 18 with distal tip portion 20 and a needle hub 22. The hollow needle 18 is affixed within the needle hub 22. The needle hub 22 is provided with a female-type luer connector 24 which is designed to connect to a male-type luer connector 26 provided on the end of the syringe barrel 12. The hypodermic syringe 10 shown in the drawings is for illustrative purposes only and the syringe needle tip cap of the present invention could be used with any type of hypodermic syringe currently on the market.

Referring back to FIG. 2, the syringe needle tip cap 30 is shown having a tubular body 32 with a closed end 34. The other end 36 is open and is provided with a radially inwardly extending rim 38. The interior surface of the tubular body 32 is provided with an inwardly extending ring or lip 39. A hydrophilic absorbent core 40 of a porous plastic material is provided within the tubular body 32 abutting the ring 39 such that the ring prevents the core 40 from being pulled out of the tubular body 32. The core 40 is compressible to allow it to be positioned within the body 32 such that the inwardly extending ring 39 compresses the core 40 to provide a snug fit within the thimble cap. Obviously, the core 40 can be held in place within the thimble cap in various ways such as simply a friction fit, or said ring 39 could be non-continuous so as to provide a plurality of tabs (not shown) extending inwardly against the side of the core 40. Furthermore, core material 40 could be placed distally past the ring 39 such that the ring 39 provides a distally facing shoulder upon which the proximal edge of the core 40 rests.

The core 40 is positioned within the tip cap 30 such that an open or hollow space 42 exists therein. The inside diameter of the tubular body 32 is decreased at 44 to prevent the core 40 from being pushed further into the tubular body 32 to close open space 42. It is preferred that the tubular body 32 be made of a clear plastic material which will not react adversely to blood to allow a medical technician to visualize the placement of the needle point within the thimble cap and the attending purging of air and any blood spray into the open space of the tubular member.

The absorbent core 40 may be manufactured out of any absorbent hydrophilic material such that it has the ability to absorb liquid. A preferred absorbent material utilizes a porous plastic technology which focuses on the ability of these materials to provide flow control for liquids or gases. Controlling the flow of a liquid or gas through a plastic is a function of pore size and pore volume and by controlling these variables the hydrophobicity, hydrophilicity and self-sealing type materials can be obtained. Interflo® Technologies of Brooklyn, N.Y. manufactures such porous plastic materials and for the purposes of the present invention it is preferred that the material be hydrophilic and not self-sealing when contacted by the liquid blood. Such a hydrophilic material is desirable so that any blood spray injected into the open space 42 of the thimble cap 30 will be quickly absorbed into the core material 40 without blocking any air flow from exiting the thimble cap 30 while depressing plunger 14.

Figure 4:
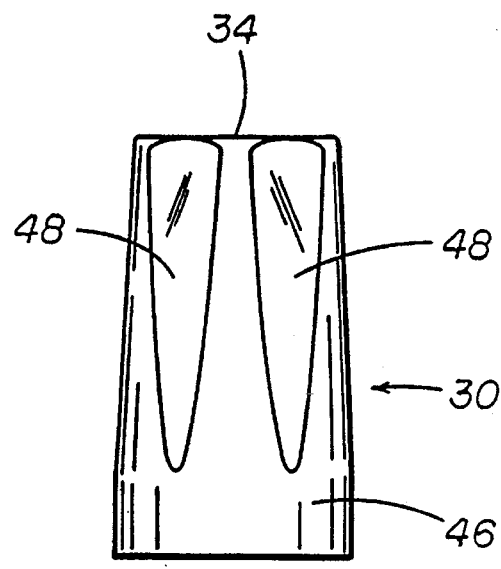
FIG. 4 is a plan view of one embodiment of the syringe needle thimble cap having a contoured outer configuration.
Figure 5:
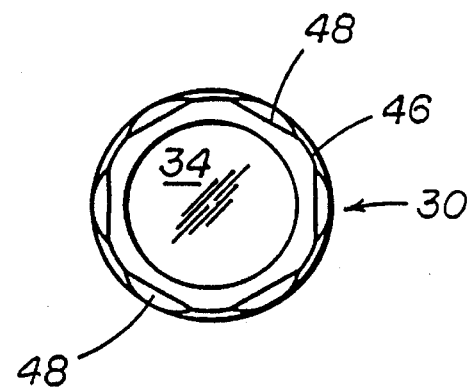
FIG. 5 is a top view of the syringe needle thimble cap shown in FIG. 4.

Referring to FIGS. 4 and 5, a preferred embodiment of the thimble cap 30 is shown having an exterior surface 46 with a plurality of flats 48 positioned about the circumference of the surface 46. The flats 48 help prevent the thimble cap 30 from rolling if placed on its side on a flat surface. Alternatively, the thimble cap 30 could have a smooth exterior surface for ease of manufacturing.

Figure 3:
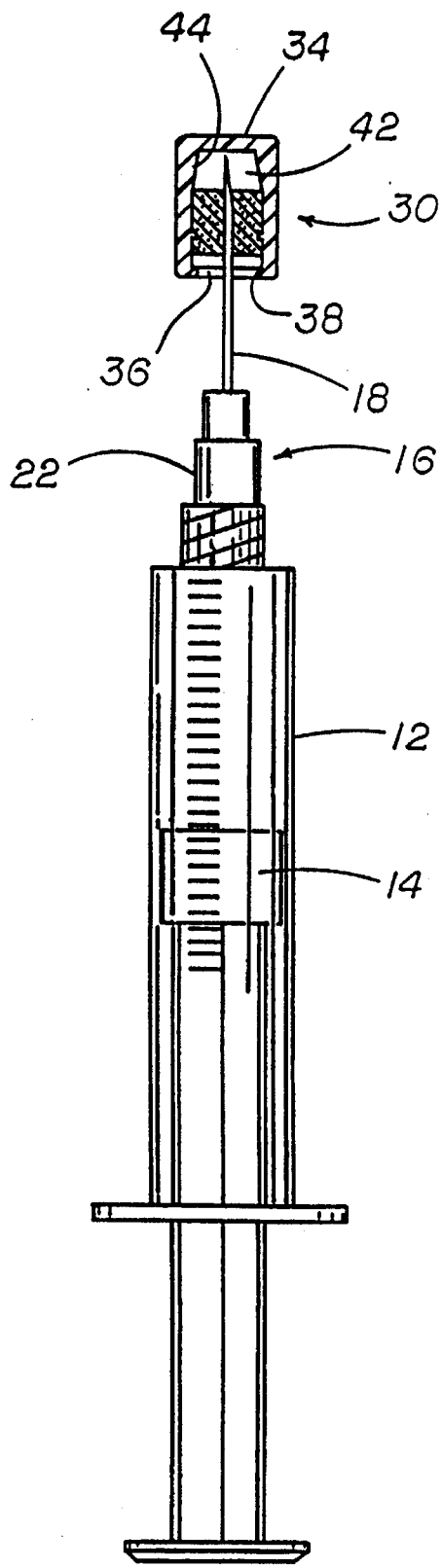
FIG. 3 is a plan view of the syringe needle thimble cap of FIG. 2 attached to the needle assembly of the syringe body shown in FIG. 1, the syringe body and needle assembly shown in the inverted position.

Operation of the syringe thimble cap in accordance with an improved method for quickly purging air bubbles from a syringe containing a patient's arterial blood gas blood sample as shown in FIGS. 1–5 will now be described with reference particularly to FIG. 3. The purpose of the improved method is to provide a syringe needle thimble cap for use with a standard syringe containing an arterial blood gas blood sample so that any air bubbles contained within the blood gas sample can be quickly purged from the syringe and needle assembly so that such air bubbles do not contaminate the results obtained from subsequent analysis of the blood sample. The syringe barrel 12 and needle assembly 16 as shown in FIG. 1 is utilized to remove a patient's blood from the patient's artery. The sharp open end of the needle assembly 16 is inserted into an artery in a patient's arm (not shown) or other injection site on the body by a qualified medical technician. The plunger 14 which had previously been inserted entirely into the syringe barrel 12 is forced back by arterial pressure or withdrawn to draw the patient's arterial blood into the syringe barrel 12. The syringe barrel 12 and needle assembly 16 is then removed by the medical technician from the patient's arm with one hand while depressing the injection site on the patient's arm or other injection site with the technician's other hand.

As is almost always the case, air will also be contained with the syringe barrel 12. In that event, the air contained within the syringe barrel 12 and needle assembly 16 must be purged as quickly as possible so that such air will not contaminate the blood sample. In particular reference to the intended purposes of the present invention, the blood sample is being taken from the patient's artery so that the patient's arterial blood gas levels can be evaluated. In taking an arterial blood gas sample, the purpose is to evaluate the patient's blood gas levels (i.e., carbon dioxide and oxygen) or to evaluate other variables which depend upon blood gas levels (i.e., pH levels, etc.), therefore the introduction of air into the blood gas sample for any significant period of time would tend to alter the true concentrations in the blood and cause subsequent analysis of this data to be misleading. In an effort to remove such air from the syringe barrel 12 and needle assembly 16 as quickly as possible, the syringe needle thimble cap 30 of the present invention is conveniently utilized as follows.

The thimble cap 30 as shown in FIG. 2 is inverted so that it is resting with its open end 36 facing upwardly on an adjoining table (not shown) to the patient and medical technician. After the syringe barrel 12 and needle assembly 16 are removed from the patient's arm as discussed above and while the technician is still depressing the patient's injection site with one hand, the technician stabs the distal tip 20 of the syringe into and through the core material 40 of the thimble cap 30. The technician then inverts the syringe barrel and needle assembly with thimble cap attached thereto such that the assembly is held as shown in FIG. 3. The syringe is then actuated by forcing its plunger 14 into the syringe barrel 12, with the needle assembly 16 being in a generally upward direction such that any air within the barrel 12 and needle assembly 16 is adjacent to and will be ejected through the needle assembly 16 and needle 18 and into the open space 42 of the thimble cap 30 from the barrel 12. Obviously, some portion of the patient's liquid blood contained within the syringe barrel 12 and needle assembly 16 will also be ejected into the open space 42 of the thimble cap 30. The blood will then be absorbed into the core material 40 to prevent blood contamination of the surgical field or the medical technician. It is not necessary or required that the needle tip extend actually into the open space 42 of the thimble cap 30 prior to depression of the plunger, however it is preferred to provide maximum protection to the medical technician and surgical field from blood contamination.

The technician can then set the syringe aside so that the technician can properly bandage the patient's injection site. The distal needle tip portion 20 is covered by the thimble cap 30, thereby protecting the medical technician against an accidental needle stick. When the technician is finished bandaging the patient's injection site, the technician can remove by rotation of the needle hub 22 from the syringe barrel 12 for proper disposal into a sharps container. A protective cap (not shown) can be twisted over the syringe barrel luer connector 26 to prevent air from reentering the syringe barrel 12 to possibly contaminate the arterial blood gas sample. The blood filled syringe barrel 12 may then be transported to the lab for proper analysis of the patient's blood gas levels as discussed earlier.

An alternate method for quickly purging air bubbles from the syringe includes changing the steps so that the medical technician stabs the distal tip 20 of the syringe into and through the absorbent core material 40 of the thimble cap 30 with one hand while depressing the injection site with the technician's other hand as discussed above. However at this point, the technician can set the syringe aside so that the patient's injection site can be properly bandaged. The medical technician then would invert the syringe barrel 12 and needle assembly 16 with thimble cap 30 impaled thereon as shown in FIG. 3. The syringe plunger 14 could then be depressed into the syringe barrel 12 to eject any air and some blood spray into the open space 42 of the thimble cap 30. And, as discussed above, the liquid blood sprayed into the thimble cap 30 would be absorbed into the core material 40 so that at no time would the patient's blood come in contact with the surgical field or the medical technician. The needle assembly 16 with thimble cap 30 protecting its distal tip portion 20 can now be removed from the syringe barrel for proper disposal into a sharps container. A protective cap (not shown) can be twisted over the luer connector 26 of the syringe barrel to prevent air from re-entering the syringe barrel and for transportation of the blood sample to the lab.

The above invention has been described in relation to a hypodermic syringe used in taking an arterial blood gas sample. However, the syringe needle thimble cap 30 could be utilized with any liquid filled syringe where air bubbles might be present and it is desirable to remove such air bubbles without having the liquid contained within the syringe be exposed exteriorly to the syringe or present a danger to any medical personnel either operating or being near the syringe or patient.

Of course, it should be understood that various other changes and/or modifications to the preferred embodiment described above or its method of use will be apparent to those skilled in the art. For example, the thimble cap 30 could have various shapes and inside configurations which still allow the thimble cap to absorb any liquid contaminate while permitting any air to be expelled from the thimble cap. Furthermore, the applicability of the invention need not be restricted to procedures involving liquid blood. Obviously, many types of hazardous liquids may be handled by the syringe needle thimble cap and its method of use. These and other changes can be made without departing from the spirit and scope of the invention and without diminishing its attendant advantages. It is therefore intended that such changes and modifications be covered by the following claims.

We claim:

1. A syringe needle thimble cap for purging air from a hypodermic needle and syringe comprising:

a cylindrical member having a closed end and an open end;

an absorbent core material affixed within said cylindrical member, the core filling only a portion of said tubular member such that an open space exists between the core and the closed end, the core being pierceable by the hypodermic needle to allow for the purging of air from the needle and syringe, the core material being hydrophilic such that it absorbs any liquid ejected from the hypodermic needle and syringe while allowing air to escape from the open space within the tubular member to the outside atmosphere.

2. A syringe needle thimble cap of claim 1, wherein the hydrophilic core is manufactured out of a porous plastic material which allows for the passage of air but not liquid.

3. A syringe needle thimble cap of claim 1, wherein the hydrophilic core is manufactured from a porous plastic material which allows for the passage of air while absorbing any liquid.

4. A syringe needle thimble cap of claim 1, wherein the cylindrical member is provided with a smooth cylindrical outside surface.

5. A syringe needle thimble cap of claim 1, wherein the cylindrical member has an exterior surface provided with a plurality of flats to prevent the cap from rolling when placed on its side.

6. A syringe needle thimble cap of claim 1, wherein said cylindrical member is made from a visually clear material to allow an intended user to observe when all of the air has been purged from the hypodermic needle and syringe.

7. A syringe needle thimble cap of claim 1, wherein the cylindrical member has an inwardly radially extending ring such that said absorbent core material is inserted within said cylindrical member so that said ring compresses against said core material to affix said core material in position within the cylindrical member.

8. A syringe needle thimble cap of claim 1, wherein the open end of said cylindrical member has an inwardly radially extending rim partially closing such open end.

9. A syringe needle thimble cap of claim 1, wherein the closed end of the cylindrical member has a relatively flat outer surface to allow said thimble cap to be easily placed on a flat surface with said open end facing in an upwardly direction.

10. A method for quickly purging air from a hypodermic syringe and needle assembly containing a blood sample, comprising the steps of:

providing a hypodermic syringe and needle assembly containing a blood sample, the hypodermic syringe having a barrel and plunger;

inserting the needle end of the hypodermic syringe and needle assembly into a syringe needle thimble cap having a tubular member with a closed end and an open end, the thimble cap being provided with an absorbent core material affixed within the tubular member adjacent its open end such that an open space exists within the tubular member between the core material and the closed end of the tubular member, the core material being pierceable by the tip of the hypodermic needle;

inverting the syringe barrel and needle assembly with thimble cap impaled thereon such that the needle assembly is pointing in an upwardly direction; advancing the plunger within the syringe to expel any air and excess blood within the syringe barrel and needle assembly into the thimble cap;

removing the needle assembly with thimble cap impaled thereon from the syringe barrel; and disposing of the needle assembly and thimble cap into a protective container.

11. The method of claim 10, wherein the inserting step includes the step of inserting the tip of the needle through the core material so that the tip of said needle extends into the interior open space within the thimble cap.

12. The method of claim 11, wherein the blood sample is an arterial blood gas sample.

13. The method of claim 10, wherein the advancing step includes the step of advancing the plunger within the syringe to expel air and blood from within the syringe barrel and needle assembly until observing a visual indication of blood being absorbed by the absorbent core material of the thimble cap.

14. A method for quickly purging air from a hypodermic syringe and needle assembly containing an arterial blood gas sample taken from a human patient by a medical technician, the syringe having a barrel and plunger, the needle assembly having a sharp needle tip, comprising the steps of:

inserting the needle tip of the hypodermic syringe and needle assembly into an artery of a human patient and obtaining an arterial blood gas sample;

removing the syringe and needle assembly from the injection site by the medical technician with one hand while depressing the injection site with the fingers of the other hand;

inserting the needle end of the syringe and needle assembly into a syringe needle thimble cap by the use of one hand of the medical technician while continuing to depress the injection site with the other hand, the thimble cap having a tubular member with a closed end and an open end, the thimble cap being provided with an absorbent core material affixed within the tubular member adjacent its open end such that a hollow space exists within the tubular member between the core material and closed end of the tubular member, the core material being pierceable by the hypodermic needle;

inverting the syringe barrel and needle assembly with thimble cap impaled thereon so that the thimble cap is above the syringe barrel by the use of one hand of the medical technician while continuing to depress the injection site with the technician's other hand;

advancing the plunger within the syringe to expel any air and excess blood from within the syringe barrel and needle assembly into the hollow space of the thimble cap by the use of one hand of the medical technician while continuing to depress the injection site with the technician's other hand;

setting the syringe barrel and needle assembly aside while cleaning and bandaging the injection site;

removing the needle assembly with thimble cap impaled thereon from the syringe barrel and disposing of the needle assembly and thimble cap into a protective container; and transporting the blood filled syringe barrel to the lab for proper analysis of the patient's blood gas levels.

15. The method of claim 14, wherein the inserting step includes the step of the core material being pierceable by the hypodermic needle so that the tip of said needle extends into the hollow space within the thimble cap.

16. The method of claim 14, wherein the step of removing the needle assembly with thimble cap impaled thereon from the syringe barrel is performed immediately before the step of setting the syringe barrel and needle assembly aside while cleaning and bandaging the injection site.

17. The method of claim 14, wherein the advancing step includes the step of advancing the plunger within the barrel to expel air and blood from within the syringe barrel and needle assembly until observing a visual indication of blood being absorbed into the core material of the thimble cap.

18. A method for quickly purging air from a hypodermic syringe and needle assembly containing an arterial blood gas sample by a medical technician using only one hand, the syringe having a barrel and plunger, the needle assembly having a sharp needle tip, comprising the steps of:

providing a syringe containing an arterial blood gas sample;

inserting the needle end of the hypodermic syringe and needle assembly into a syringe needle thimble cap having a tubular member having a closed end and an open end, the thimble cap being provided with an absorbent core material affixed within the tubular member adjacent its open end such that an open space exists within the tubular member between the core material and the closed end thereof, the thimble cap resting on an adjoining surface with its open end facing upwards, the core material being pierceable by the needle so that the needle tip extends into the open interior space within the thimble cap;

inverting the syringe barrel and needle assembly with the thimble cap impaled thereon such that the needle assembly is pointing in an upwardly direction; and advancing the plunger within the syringe to expel any air and excess blood within the syringe barrel and needle assembly into the thimble cap.

19. The method of claim 18, wherein the advancing step includes the step of advancing the plunger within the syringe barrel to expel any air and blood from within the syringe barrel and needle assembly until observing a visual indication of blood being absorbed into the core material of the thimble cap.

* * * * *